(12) United States Patent
King et al.

(10) Patent No.: US 10,744,646 B2
(45) Date of Patent: Aug. 18, 2020

(54) CAMERA CONTROL SYSTEM AND METHOD

(71) Applicant: Wayne State University, Detroit, MI (US)

(72) Inventors: Brady W. King, Clinton Township, MI (US); Luke A. Reisner, Madison Heights, MI (US); Anthony M. Composto, Sterling Heights, MI (US); Abhilash K. Pandya, Grosse Ile, MI (US); Richard D. Ellis, Canton, MI (US); Michael D. Klein, Grosse Pointe, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 14/913,793

(22) PCT Filed: Aug. 29, 2014

(86) PCT No.: PCT/US2014/053447
§ 371 (c)(1),
(2) Date: Feb. 23, 2016

(87) PCT Pub. No.: WO2015/031777
PCT Pub. Date: Mar. 5, 2015

(65) Prior Publication Data
US 2016/0279799 A1    Sep. 29, 2016

Related U.S. Application Data

(60) Provisional application No. 61/871,490, filed on Aug. 29, 2013.

(51) Int. Cl.
*G06F 19/00*     (2018.01)
*B25J 9/16*      (2006.01)
(Continued)

(52) U.S. Cl.
CPC ............. *B25J 9/1697* (2013.01); *A61B 34/30* (2016.02); *A61B 90/361* (2016.02);
(Continued)

(58) Field of Classification Search
CPC ..... B25J 9/1697; B25J 9/1679; H04N 5/2253; H04N 5/23296; G05B 2219/40584
(Continued)

(56) References Cited

U.S. PATENT DOCUMENTS

| 5,384,594 A | 1/1995 | Sieber et al. |
| 5,417,210 A | 5/1995 | Funda et al. |

(Continued)

FOREIGN PATENT DOCUMENTS

| WO | 2012065175 A9 | 5/2002 |
| WO | 2007/030173 A1 | 3/2007 |

(Continued)

OTHER PUBLICATIONS

United States Patent and Trademark Office, Alexandria, Virginia, International Search Report of International Application No. PCT/US2014/053447, dated Nov. 24, 2014, 2 pages.
(Continued)

*Primary Examiner* — Ronnie M Mancho
(74) *Attorney, Agent, or Firm* — Fishman Stewart PLLC (57) ABSTRACT

A system and method for automatically operating a camera includes a controller for controlling the movement of a robotically controlled camera. The controller includes a processor and a computer readable medium having instructions for controlling the camera. The system determines a task to be performed and, based on the determined task, determines a camera control scheme that corresponds to the task. The camera control scheme includes rules for controlling the camera. The system receives input parameters in the form of particular tools being used and the position and
(Continued)

movement of the tools. The input parameters can be automatically determined by the controller via a video image produced by the camera. The controller will move the camera in response to particular movement of the tools and the particular rules of the determined control scheme that correspond to the particular movements.

18 Claims, 6 Drawing Sheets

(51) Int. Cl.
    *A61B 90/00*     (2016.01)
    *A61B 34/30*     (2016.01)
    *H04N 5/225*     (2006.01)
    *H04N 5/232*     (2006.01)

(52) U.S. Cl.
    CPC .......... *B25J 9/1679* (2013.01); *H04N 5/2253* (2013.01); *H04N 5/23296* (2013.01); *A61B 2090/373* (2016.02); *G05B 2219/40584* (2013.01)

(58) Field of Classification Search
    USPC .................................................. 700/245, 259
    See application file for complete search history.

(56) References Cited

U.S. PATENT DOCUMENTS

| | | |
|---|---|---|
| 5,545,120 A | 8/1996 | Chen et al. |
| 5,820,545 A | 10/1998 | Arbter et al. |
| 6,097,423 A | 8/2000 | Mattsson-Boze et al. |
| 6,471,637 B1 | 10/2002 | Green et al. |
| 6,663,559 B2 | 12/2003 | Hale et al. |
| 6,926,709 B2 | 8/2005 | Bieger et al. |
| 7,134,992 B2 | 11/2006 | Schara et al. |
| 7,585,273 B2 | 9/2009 | Adler et al. |
| 7,833,152 B2 | 11/2010 | Chatenever et al. |
| 8,073,528 B2 | 12/2011 | Zhao et al. |
| 8,679,096 B2 * | 3/2014 | Farritor ............... A61B 19/2203 606/1 |
| 9,579,088 B2 * | 2/2017 | Farritor ............ A61B 17/00234 |
| 2002/0156345 A1 | 10/2002 | Eppler et al. |
| 2004/0010190 A1 | 1/2004 | Shahidi |
| 2008/0082109 A1 | 4/2008 | Moll et al. |
| 2008/0221591 A1 | 9/2008 | Farritor et al. |
| 2009/0036902 A1 * | 2/2009 | DiMaio ............... A61B 19/2203 606/130 |
| 2009/0088897 A1 | 4/2009 | Zhao et al. |
| 2009/0240371 A1 * | 9/2009 | Wang ...................... B25J 9/1689 700/259 |
| 2009/0270678 A1 * | 10/2009 | Scott .................. A61B 1/00009 600/109 |
| 2010/0274087 A1 | 10/2010 | Diolaiti et al. |
| 2011/0028992 A1 | 2/2011 | Geiger et al. |
| 2011/0187875 A1 * | 8/2011 | Sanchez .................. A61B 34/35 348/207.11 |
| 2013/0066304 A1 * | 3/2013 | Belson ............. A61B 17/00234 606/1 |
| 2013/0066335 A1 | 3/2013 | Barwinkel et al. |
| 2013/0293362 A1 * | 11/2013 | Parazynski ............ G08C 19/16 340/12.52 |
| 2013/0331644 A1 * | 12/2013 | Pandya .................. B25J 9/1682 600/102 |
| 2014/0018819 A1 * | 1/2014 | Raj ........................ A61B 34/70 606/130 |

FOREIGN PATENT DOCUMENTS

| | | |
|---|---|---|
| WO | 2008/031077 A2 | 3/2008 |
| WO | 2008031077 A3 | 3/2008 |
| WO | 2010/117685 A2 | 10/2010 |
| WO | 2012/044334 A2 | 4/2012 |
| WO | 2012/065175 A2 | 5/2012 |
| WO | 2012/078989 A1 | 6/2012 |

OTHER PUBLICATIONS

Golenberg, Lavie P., "Task analaysis, modeling, and automatic identification of elemental tasks in robot-assisted lapar, oscopic surgery", Jan. 1, 2010, ETD Collection for Wayne State University, Paper AAI3427271.

Lin H.C, Shafran I, Yuh D., Hager G.D., "Towards automatic skill evaluation: Detection and segmentation of robot-assisted surgical motions," Computer Aided Surgery, vol. 11, pp. 220-230, 2006.

Reiley CE, Lin HC, Varadarajan B, Vagvolgyi B, Khudanpur S, Yuh DD, Hager GD (2008) Automatic recognition of motions using statistical modeling for capturing variability. Stud Health Technol Inform 132(1):396-401.

Padoy N., Blum T., Feussner H., Berger M-O., Navab N., "A Boosted Segmentation Method for Surgical Workflow Analysis," in Medical Image Computing and Computer-Assisted Intervention—MICCAI 2007, ed, 2007, pp. 102-109.

Padoy N., Blum T., Feussner J., Berger M-O., Navab N., "On-line Recognition of Surgical Activity for Monitoring in the Operating Room," in 20th Conference on Innovative Applications of Artificial Intelligence—IAAI'08, Chicago, IL, 2008, pp. 1718-1724.

Reiley C.E. And Hager G.D., "Task versus Subtask Surgical Skill Evaluation of Robotic Minimally Invasive Surgery," presented at the Proceedings of the 12th International Conference on Medical Image Computing and Computer-Assisted Intervention: Part 1 London, UK, 2009.

Varadarajan B., Reiley C., Lin H., Khudanpur S., Hager G. (2009) Data-Derived Models for Segmentation with Application to Surgical Assessment and Training. In: Yang GZ., Hawkes D., Rueckert D., Noble A., Taylor C. (eds) Medical Image Computing and Computer-Assisted Intervention—MICCAI 2009. MICCAI 2009. Lecture Notes in Computer Science, vol. 5761. Springer, Berlin, Heidelberg.

T.E. Murphy, "Towards Objective Surgical Skill Evaluation with Hidden Markov Model-based Motion Recognition," Masters of Science, Mechanical Engineering, Johns Hopkins University, Baltimore, 2004.

Speidel S., Delles M., Gutt C., Dillmann R. (2006) Tracking of Instruments in Minimally Invasive Surgery for Surgical Skill Analysis. In: Yang GZ., Jiang T., Shen D., Gu L., Yang J. (eds) Medical Imaging and Augmented Reality. MIAR 2006. Lecture Notes in Computer Science, vol. 4091. Springer, Berlin, Heidelberg.

Lin H.C., Shafran I., Murphy T.E., Okamura A.M., Yuh D.D., Hager G.D. (2005) Automatic Detection and Segmentation of Robot-Assisted Surgical Motions. In: Duncan J.S., Gerig G. (eds) Medical Image Computing and Computer-Assisted Intervention—MICCAI 2005. MICCAI 2005. Lecture Notes in Computer Science, vol. 3749. Springer, Berlin, Heidelberg.

Wei G-Q, Arbter K, Hirzinger G. Automatic Tracking of Laparoscopic Instruments by Color Coding. Lecture Notes in Computer Science. 1997;1205/1997:357-66.

Fortnoy, DR, "Real-Time Color Image Guidance System," for the Dept. of Electrical and Computer Engineering, University of California, Feb. 2000, Santa Barbara, Calif.

Lee C., Wang YF, Uecker DR, Wang Y. Image Analysis for Automated Tracking in Robot-Assisted Endoscopic Proceedings of 12th International Conference on Pattern Recognition. 1994; 1:88-92.

Wei, G-Q, Arbter K; Hirzinger, G. Real-Time Visual Servoing for Laparoscopic Surgery. Controling robot motion with color image segmentation. Engineering in Medicine and Biology Magazine, IEEE. 1997;16(1):40-5.

Omote K., Feussner H, Ungeheuer A., Arbter K, Wei G-Q, Siewert J., et al., "Self-Guided Robotic Camera Control for Laparascopic Surgery Compared with Human Camera Control," for the American Journal of Surgery, 1999, vol. 177, Apr. 1999, pp. 321-324.

(56) References Cited

OTHER PUBLICATIONS

Ko S-Y, Kim J, Lee W-J Lee, Kwon D-. Compact laparoscopic assistant robot using a bending mechanism. Advanced Robotics. 2007; 21:5-6, 689-709.

Casals A., Amat J., Laporte E, editors., "Automatic Guidance of an Assistant Robot in Laparoscopic Surgery", Proceedings of the 1996 IEEE International Conf. on Robotics and Automation; Apr. 1996; Minneapolis, Minnesota, pp. 895-900.

Uecker D.R., Wang Y. F., Lee Cheolwhan, Wang Yulun. Automated Instrument Tracking in Robotically Assisted Laparoscopic Surgery, Journal of Image Guided Surgery, 1995; 1:6, 308-325.

Ko, Seong Young, Kwon, D-S, "A Surgical Knowledge Based Interaction Method for a Laparoscopic Assistant Robot," 13th IEEE International Workshop on Robot and Human Interactive Communication, 2004, Kurashiki, Okayama Japan.

\* cited by examiner

CAMERA CONTROL SYSTEM AND METHOD

BACKGROUND

1. Field of the Invention

The present invention relates generally to an automatically controlled camera and, more specifically, to an autonomously controlled camera that is context adaptive.

2. Description of Related Art

Camera systems are in widespread use in various workspaces. These camera systems are used, for example, to record and document a procedure being performed for review and monitoring after the procedure, or to visualize a procedure concurrent with the performance of the procedure. One type of field in which camera use is widespread is the field of medical procedures.

Camera use in medical procedures commonly involves manipulating a camera to record and document the procedure being performed, as well as providing visualization of a surgical site that is other wise obscured, such as minimally invasive surgical procedures. One type of minimally invasive surgery is laparoscopy, where surgical tools are inserted into a patient's body cavity through small incisions near the target area for surgery. These small incisions are large enough to allow the surgical tool to be inserted, but not large enough to allow for the surgeon to directly view the surgical site. Accordingly, a camera is also inserted into the surgical site, either through an additional small incision or endoscopically through an orifice in the patient's body and through the body toward the surgical site.

However, viewing the surgical site through the camera involves manipulation of the camera manually by the surgeon performing the procedure. Alternatively, manipulation of the camera can be performed by another person acting as the camera operator. The camera operator may take direction from the surgeon, or may move the camera manually without instruction by the surgeon. Robotic cameras are used in some procedures, but the robots also require manipulation by a surgeon or another user to receive instructions on where and how to operate.

However, in each of these situations, manipulation of the camera is inefficient. The surgeon needs to pause the procedure to move the camera to the desired view every time a new view is desired. Or, the surgeon needs to issue commands to the operator who needs to receive the commands and move the camera to the desired location based on the surgeon's instructions. This may require additional manipulation if the operator does not move the camera to a location suitable to the surgeon. In issuing commands, the surgeon has to direct his attention away from the procedure. If the operator moves the camera independently of the surgeon's commands, the operator may move the camera to an undesired location, thereby requiring correction at the direction of the surgeon.

Furthermore, due to the inefficiency of having to stop a procedure to move the camera, a surgeon may choose to continue a procedure using a suboptimal camera angle rather than pause to move the camera. Operating with a suboptimal camera angle can also lead to inefficiencies or inaccuracies, ultimately requiring movement anyway, or repeated attempts of the procedure.

Accordingly, improvements can be made to the control of cameras in surgical procedures and other procedures where camera use is beneficial.

SUMMARY

A system for automatically controlling a camera is provided. The system includes a controller in the form of a computing device including a processor and a computer readable medium having instructions stored thereon and a robotic mechanism operatively coupled to the controller that receives commands from the controller for manipulating a camera coupled to the robotic mechanism. The controller determines a task to be performed based on first input parameters received at the controller. The controller automatically determines a pre-determined control scheme corresponding to the determined task. The control scheme includes pre-determined rules for controlling the robotic mechanism. The controller further receives second input parameters. The robotic mechanism automatically performs at least one adjustment corresponding to the pre-determined rules in response to the controller receiving second input parameters.

In another aspect of the invention, a method for automatically controlling the movement of a camera is provided. The method includes the steps of receiving, at a controller comprising a computer device having a processor and a computer readable medium having instructions stored thereon, first input parameters; determining, at the controller, a pre-defined task to be performed based on the input parameters; determining, at the controller, a pre-defined control scheme corresponding to the task, wherein the pre-defined control scheme includes a plurality of pre-defined rules; receiving, at the controller, second input parameters; determining, at the controller, a movement command based on the second input parameters, wherein the movement command corresponds to an individual rule of the plurality of pre-defined rules, wherein the individual rule is determined based on the second input parameters; and automatically moving a robotic mechanism in accordance with the movement command.

Additional benefits and advantages of the present invention will become apparent to those skilled in the art to which the present invention relates from the subsequent description of the preferred embodiment and the appended claims, taken in conjunction with the accompanying drawings.

BRIEF DESCRIPTION OF THE DRAWINGS

The accompanying drawings incorporated in and forming a part of the specification illustrate several aspects of the present invention, and together with the description serve to explain the principles of the invention. In the drawings.

DESCRIPTION OF SPECIFIC EMBODIMENTS

Figures 1, 2:
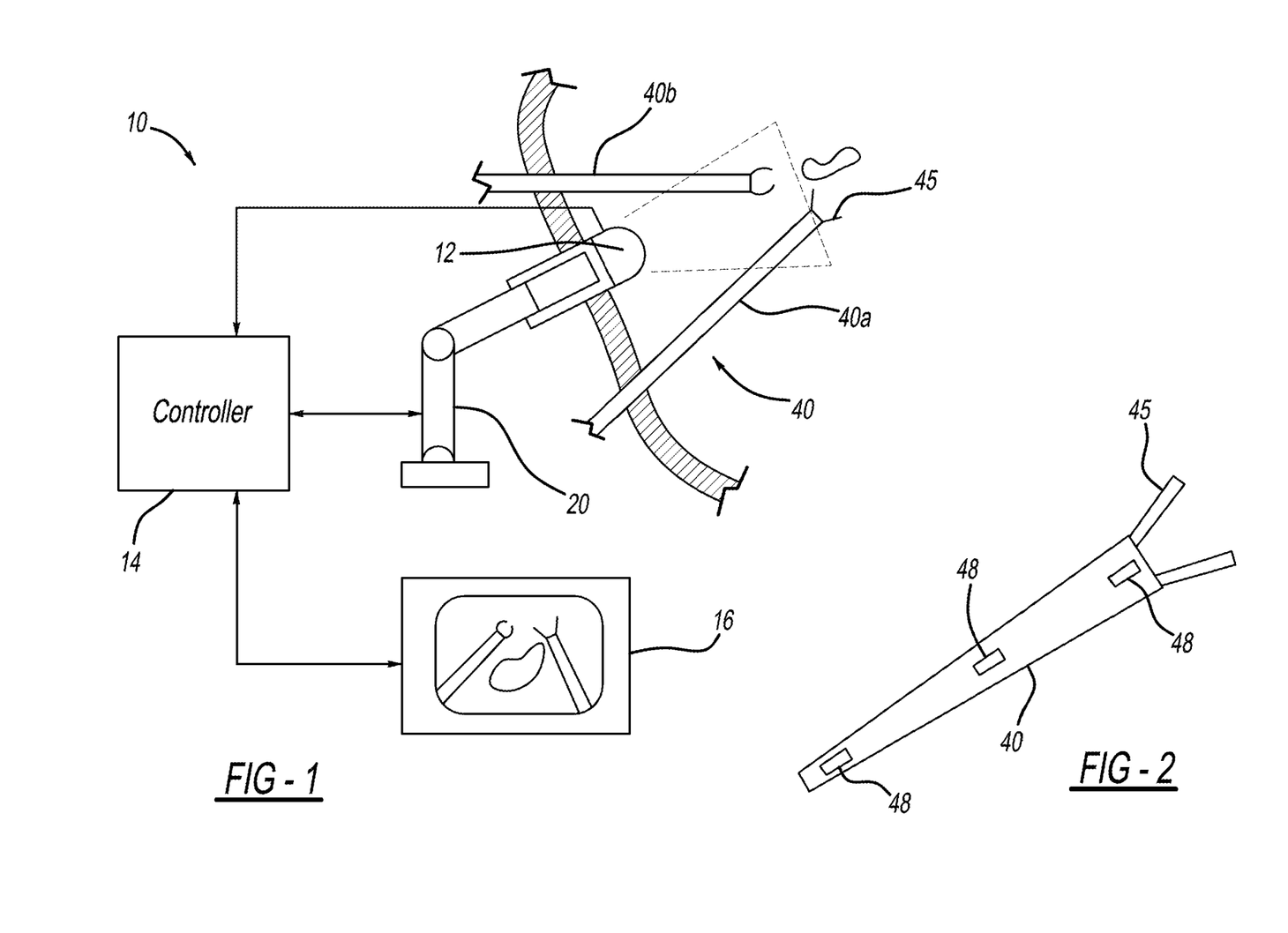
FIG. 1 is a schematic view of a camera control system, including a controller, a robot, a camera, a video monitor, and tools for performing a procedure.
FIG. 2 is a schematic view of the one of the tools having detectable elements.

Turning now to FIGS. 1-8, a system 10 for automating camera movement is provided. With reference to FIG. 1, the system 10 includes a camera 12 that is configured to be adjusted in response to signals received from a controller 14. The controller 14 includes a computing device having a processor and a computer readable medium having instructions stored thereon that, when executed by the computing device, cause the camera 12 to be adjusted.

The descriptions herein will be primarily directed to the use of a camera in a surgical setting using medical devices. However, it will be appreciated that the described system 10 can also be used in other non-surgical or non-medical settings where automatic camera control is desired, such as for mechanical repairs of automobiles, aircraft, or the like. It can also be used in other remote applications such as underwater applications or in outer space. It can be used for procedures involving the handling of chemicals or other hazardous material where remote procedures are beneficial. Other applications will become apparent to persons having skill in the art.

The camera 12 is adjustable in its position and orientation in response to signals from the controller 14. For example, the camera 12 is adjustable along three orthogonal axes, such as the X, Y, and Z axes. The camera 12 is further adjustable via rotation about its longitudinal axis. The camera 12 is also adjustable via zooming in and out to increase or decrease the camera's field of view, as well as having an adjustable focus in order to focus on objects both near and far from the camera, as desired.

Accordingly, the camera 12 is moveable in and out, side to side, up and down, and around its longitudinal axis. The camera 12 is also adjustable while remaining stationary, by zooming in and out and adjusting its focus. Simply put, the camera 12 is capable of being manipulated in the same ways as manually adjustable camera.

The system 10 further includes a video monitor 16 that displays the field of view of the camera 12. The monitor 16 will display the video outputs of the camera 12 via the controller 14 to allow the user of the system 10 to watch as the camera 12 is adjusted to modify the view. The monitor 16 can also display other information associated with the camera 12 and its operating environment. The monitor 16 is also adjustable by the controller 14 to digitally zoom in addition to or as an alternative to the optical zooming capabilities of the camera 12. The monitor 16 can further adjust the view to account for changes in the "horizon" of the view. For example, if the camera 12 has rotated around its axis, the horizon may appear at an angle or inverted relative to an expected horizon. Rather than adjust the orientation of the camera 12 about its axis, the monitor 16 can digitally adjust the output to correct for askew horizons. This can allow the user of the system 10 to be able to view the worksite more naturally. For instance, as the camera 12 moves, the image that is output from the camera 12 could result in tools operated by the user's right hand being on the left side of the screen. This can be corrected by adjusting the image, so that the user's movement of tools up/down/left/right corresponds to what is displayed.

Movement of the camera 12 is preferably performed by a robot 20 that receives commands from the controller 14. The camera 12 is affixed to the robot 20 in a manner known in the art. One example of the robot is an existing surgical robot, such as Intuitive Surgical's da Vinci. Of course, any other robot 20 that provides sufficient control over the position and orientation of the camera 12 can also be used.

The system 10 is usable to aid the user with his manipulation of his tools for the selected procedure. Accordingly, the system 10 also includes one or more tools 40. It will be appreciated that tools 40 can be in the form of a variety of tools for performing various tasks and procedures. For example, in a surgical context, tools 40 can be in the form of cutting tools, suturing tools, cauterizing tools, clipping tools, delivery devices, and the like. More than one tool can be used during a particular task, and these tools may be referred to generally as 40*a*, 40*b*, etc. In many cases, two tools 40 will be used, given that a typical surgeon operates with two hands. However, more than two tools 40 could also be used in certain instances, such as where a surgeon will leave a tool in place while working with another tool, or in instances where multiple surgeons operate within the same workspace. Different tools 40 can also be removed or introduced during the procedure.

The controller 14 will output signals or commands to the camera 12 via the robot 20 to adjust the position and/or orientation of the camera 12. The signals or commands are based on determinations made by the controller 14 according, in part, to inputs received by the camera 12. In short, the view of the camera 12 and the images generated by the camera 12 and received by the controller 14 will be analyzed by the controller 14 and evaluated, and movement commands will be generated by the controller 14 based on the algorithms stored therein. The camera 12, operated by the robot 20, will move in accordance with the movement commands generated by the controller 14.

The controller 14 is programmed with various predetermined commands for operating the camera 12. The commands can include: move left, move right, move up, move down, move in, move out, pan left/right/up/down, zoom in/out, tilt, rotate, and the like. These commands can be performed alone or in combination with each other to provide a robust ability to move and adjust the camera 12 as determined by the controller 14.

The selected combination of commands is determined based on the programmed algorithms, which are predetermined based on research and studies regarding user preference and need for various procedures. For example, a laparoscopic procedure to remove a cyst may have a predetermined preference for the field of view of the tools 40 being used to remove the cyst. A procedure involving suturing may have a predetermined field of view that is more narrow and focused on the suturing site. It will be appreciated that various other procedures will have different needs and different preferred camera control schemes.

The types of procedures that can be performed for which autonomous camera control can be used are extensive. The procedures may also be referred to as subtasks. Subtasks include, but are not limited to: suturing, knot tying, clipping, cutting, dissection, exploration, insertion of a new tool, removal of a tool, stapling, specimen retrieval, cauterizing, embolizing, suction, perfusion, and fluid delivery. Multiple subtasks can be performed within a single surgery or overall task/procedure. Accordingly, these various procedures can be generally referred to as tasks, and a task can have one or more subtasks.

Depending on the task or subtask being performed, the controller 14 will determine the appropriate camera control scheme that corresponds to the subtask. There are various camera control schemes programmed into the controller 14. The same camera control scheme can be used for different subtasks, if the subtasks have similar preferred camera control needs. Additionally, a particular subtask may have more than one camera control scheme. In a preferred approach, each individual task or subtask will have an individual control scheme that corresponds to the task or subtask.

Before determining the appropriate camera control scheme, the controller 14 will determine the task or subtask being performed. The task or subtask being performed can be determined in multiple ways. Generally, the task or subtask being performed is based on received input parameters.

The user can manually input the subtask into the controller 14 via a user interface, in one approach. This can be done via manual switch on the controller, by selecting from a list on a graphical user interface, by voice control, or by any other known manual input method. In this approach, the manual input is the input parameter that determines the task or subtask.

In another approach, the task or subtask can be automatically determined by the controller 14 by an algorithm programmed into the controller 14. In this approach, the controller 14 will analyze various characteristics of the procedure, such as the tools 40 being used, the surgeon performing the procedure, and/or the movements of the tools 40. In one approach, the controller 14 will analyze the video output of the camera 12, which includes the tools 40 in the field of view. The controller 14 will analyze the image using image analysis software to determine the tools 40 that are being used. The controller 14 can additionally or alternatively analyze areas of interest within the field of camera 12, such as particular organs or diseased body parts. Accordingly, in this approach, the input parameters for determining the subtask are the tools 40 or other objects within the field of view of the camera 12 that are analyzed and determined by the controller 14. In this approach, the controller 14 can detect multiple tasks that are performed in sequence, in accordance with tool changes or anatomical changes as a result of a completed procedure.

Once the particular subtask has been determined by the controller 14, either manually or automatically, the controller 14 will determine the camera control scheme to be used. The camera control scheme associated with individual subtasks are optimized for the subtask. The control schemes apply rules using various parameters to dictate when, where, and how the camera is moved. For example, in a particular subtask, the camera may begin in a stationary position, and remain stationary for a set amount of time. It may subsequently move forward the target site via the robot, at which point it will zoom out to increase the field of view. It will be appreciated that various other types of camera movement can be controlled according to various parameters.

The rules comprise the algorithm that will ultimately determine the commands that are sent to the camera 12 via the robot to automatically control the movement of the camera. It will be appreciated that the rules of the algorithm can be complex and include various conditions and dependent conditions. In response to input parameters that are received by the controller 14 via the camera 12, such as tool position or movement within the field of view, the rules of the control scheme will be applied in accordance with the programmed algorithm.

The parameters that determine how the camera is moved can be divided into two groups: input parameters and movement parameters. Input parameters include, but are not limited to, position and orientation of one or more tools 40. Position and orientation can be determined as camera image coordinates, which is the position of the tools 40 within the view of the camera, or as 3D world coordinates, which is the position of the tools 40 independent of the camera image, for example when the tools 40 are off-screen. Of course, 3D world coordinates can also be used while the tools 40 are on-screen.

Further input parameters include the position/orientation of one or more points/regions/objects of interest. The points can be designated by the user or determined automatically based on image processing or scene analysis performed by the controller 14. For example, the controller 14 may analyze the image and determine the position of a particular organ or body vessel. Or, the user can designate an object of interest manually via a user interface.

Other input parameters include the insertion points of the tools 40, or the status of one or more end-effector 45 of the tools 40. End effectors 45, illustrated schematically in FIGS. 1 and 2, can include, for example, grasping claws, pincers, or other moveable elements, or activatable elements like an electrically activatable tip for heating or cauterizing an incision, or a magnetic element, or a fluid delivery tip. It will be appreciated that other end effectors 45 can be also used depending on the type of procedure. The status of the end effectors 45 can be open, closed, activated, or the like.

In addition to the above described input parameters, the camera control scheme applies rules using movement parameters as well. Movement parameters determine how the camera 12 is moved. Some of the possible movement parameters include the typical/maximum speed of the camera movement, the typical/maximum rate of zoom level changes, the size of the dead zone, and input filtering parameters or delays before movement. The controller 14 will analyze the movement parameters to determine, based on the control scheme, the necessary movement command to arrive at the desired camera position.

The camera control schemes apply rules based on the input parameters to determine when and where to move or zoom the camera. For example, the camera 12 may follow the end effector 45 of one of the tools 40 or the centroid of multiple tools 40. For example, if the tool or tools 40 move to the left, the camera will move to the left, if desired based on the subtask and the defined camera control scheme for that subtask. However, in some control schemes for some tasks, the rule may instruct the camera 12 to remain stationary. It will be appreciated that descriptions of camera movement can also include a lack of movement or maintaining a particular position or orientation.

The zoom level may be controlled by the proximity of tools 40 to the camera or the current state of activation of the end effectors. For example, if the tools 40 are close to the camera 12, the camera 12 may zoom out in order to show more of the area surrounding the tools 40 if desired depending on the determined camera control scheme. Alternatively, if the tools 40 are relatively far away from the camera 12, the camera 12 may zoom in. Of course, if desired according to the control scheme, the camera 12 may zoom in on tools 40 that close to the camera 12, or it may zoom out if the tools 40 are far from the camera. The movement of the camera 12 will move as instructed by the rules of the control scheme based on the relative proximity of the tools 40 to the camera 12.

In addition or alternatively to zooming, the camera 12 can also move in and out to adjust the field of view. It can zoom out while moving in, or zoom in while moving out, thereby keeping the size of the tools 40 in the field of view the same, but changing the perspective of the surrounding area.

Other known camera movements are also possible, such as tilting or rotating.

The camera 12 may also remain focused on a defined or determined point of interest depending on the control scheme while continuing to track the movement of the instruments, if desired.

It will be appreciated that other possible rules for the camera control scheme could also be implemented based on the needs of the associated subtask.

Figure 3:
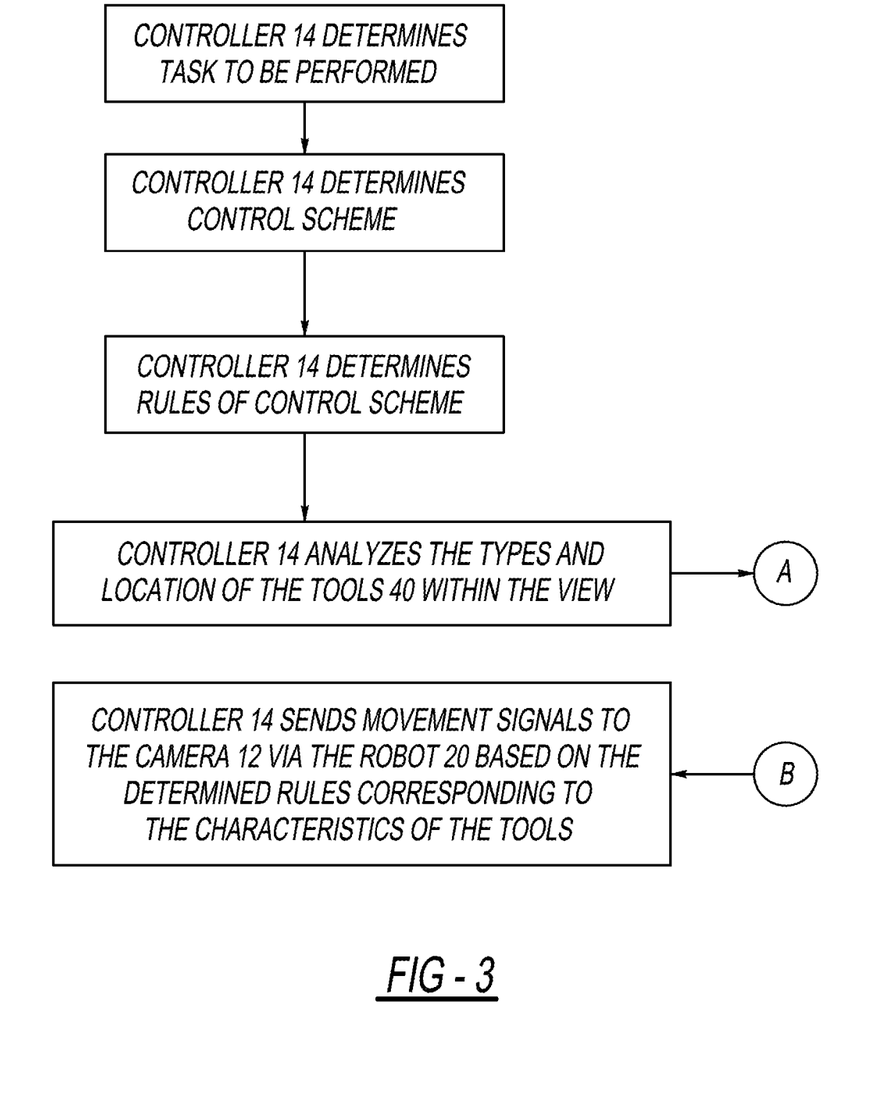
FIG. 3 is a flow chart illustrating the operation of one aspect of the system.

One example of implementing a basic camera control scheme and rules based on input parameters received at the controller 14 is illustrated in FIG. 3. The controller 14 determines the task to be performed. Based on the determined subtask, the controller 14 determines the camera control scheme that is associated with that subtask and determines the rules associated with that camera control scheme. The controller 14 analyzes the types of tools 40 and the locations of the tools 40. Based on the rules of control scheme corresponding to the determined tool characteristics, the controller 14 sends movement signals to the camera 12 via the robot 20.

One or more rules of the control scheme can be applied, which is denoted by element A in FIGS. 3-6, where element B indicates a return to the illustration of FIG. 3. Some exemplary rules are described below. It will be appreciated that various other rules for controlling the camera 12 based on input parameters, such as tool characteristics or environmental characteristics, can also be defined and programmed into the controller.

With reference to FIG. 3, the controller 14 determines that two tools 40 are in view. The controller analyzes the location of the tools 40 and determines a centroid of the tools 40. The controller 14 sends movement signals to the camera 12 via the robot 20, instructing the camera 12 to pan and tilt to locate the centroid near the center of the camera's view.

To minimize extraneous movement of the camera 12, movement of the camera 12 to track the centroid is not performed unless the centroid is sufficiently far from the center of the camera's view. For example, if the centroid is slightly to the left of center of the view, the camera 12 will not move because the centroid is sufficiently close to the center of the view such that the user can perform the desired subtask. But, if the centroid of the tools 40 is almost off the screen, the camera 12 will move to center the view of the camera on the centroid of the tools 40.

Figure 4:
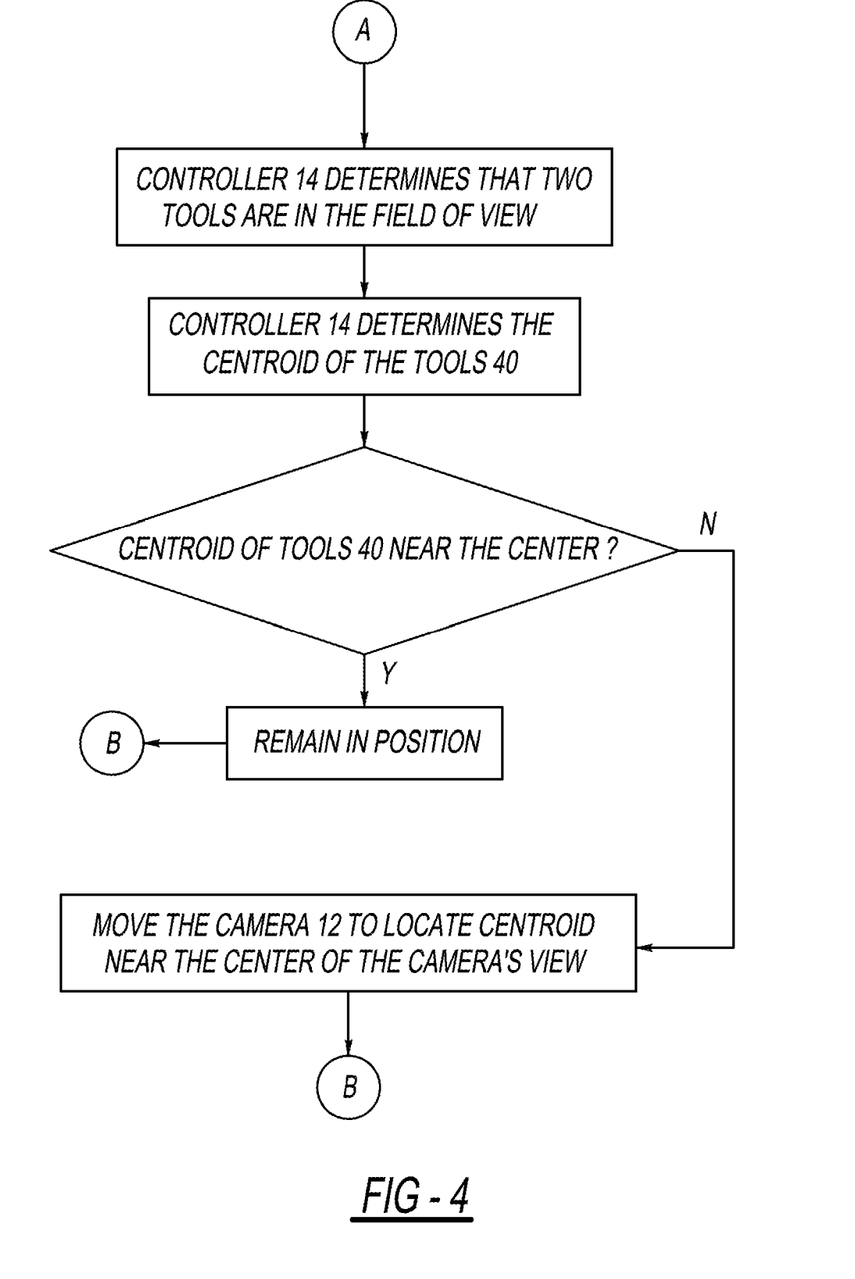
FIG. 4 is a flow chart illustrating a portion of the operation of another aspect of the system.
Figure 5:
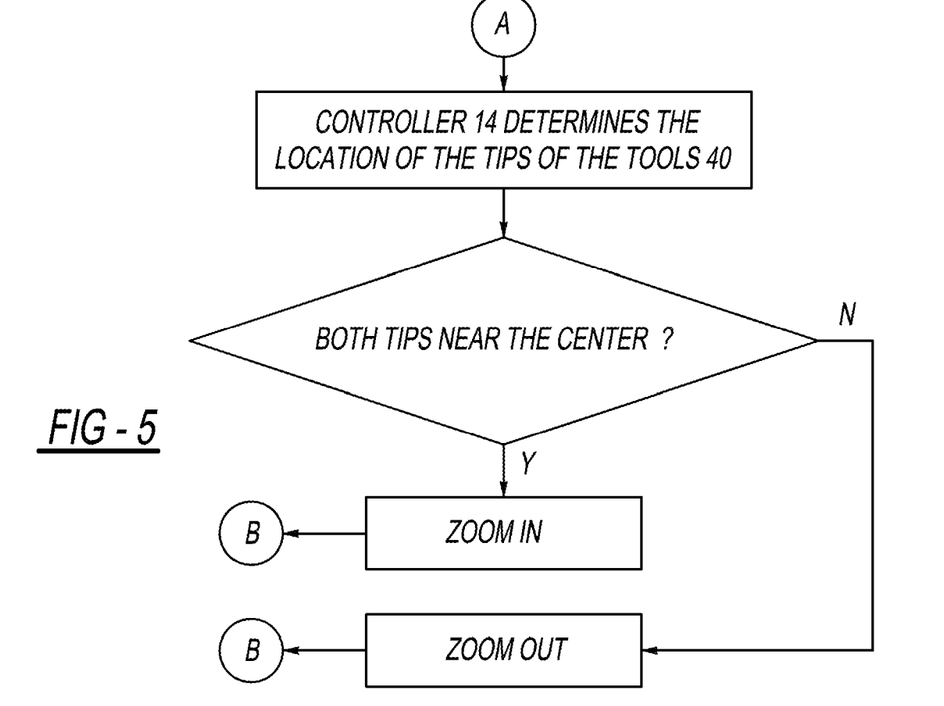
FIG. 5 is a flow chart illustrating a portion of the operation of another aspect of the system.

With reference to FIG. 4, the controller 14 will determine, in one aspect, the location of the tips of the tools 40. If both of the tips of the tools 40 are near the center of the view, the camera 12 will zoom in. When the tools 40 are each near the center of the view, that can indicate, depending on the subtask, that the user is performing a precise manipulation of the tools 40, thereby desiring a more detailed view. It can also mean that the camera 12 is relatively far from the tools 40. Conversely, if both of the tool 40 tips are not near the center but near the edge of the view, the camera 12 will zoom out. When the tools 40 are near the edge of the view, it can indicate that the tools 40 are too close to the camera 12, or it can indicate that the user is performing a procedure at points that are far away from each other.

Figure 6:
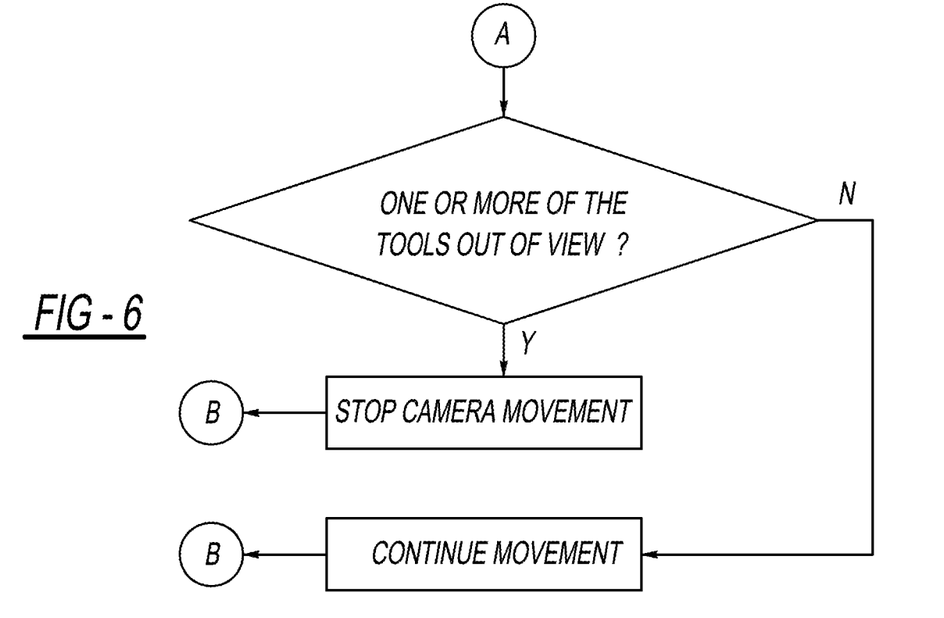
FIG. 6 is a flow chart illustrating a portion of the operation of another aspect of the system.

With reference to FIG. 6, if one of the tools 40 leaves the view, the camera 12 will stop all movement of the camera 12. When the tool 40 leaves the view, this can indicate that the procedure is over, or that the tool 40 is being removed from the target area to be replaced by another tool 40. Of course, an alternative camera control scheme may have rules that instruct the camera 12 to attempt to track the tool 40 that has left the view, depending on the subtask. For example, the user may be moving the tool 40 to an area off screen on purpose and desire that the camera 12 moves with it.

As previously described above, the controller 14 may also implement horizon correction in the event that camera 12 rotates according to the camera control scheme. Whether or not horizon correction is implemented depends on the particular camera control scheme determined to be used. The horizon can be manually entered via a user interface or automatically determined based on the initial position of the tools 40 or the detected position of the organs within the view. The horizon can also be determined based on the initial position of the camera 12.

Figure 7:
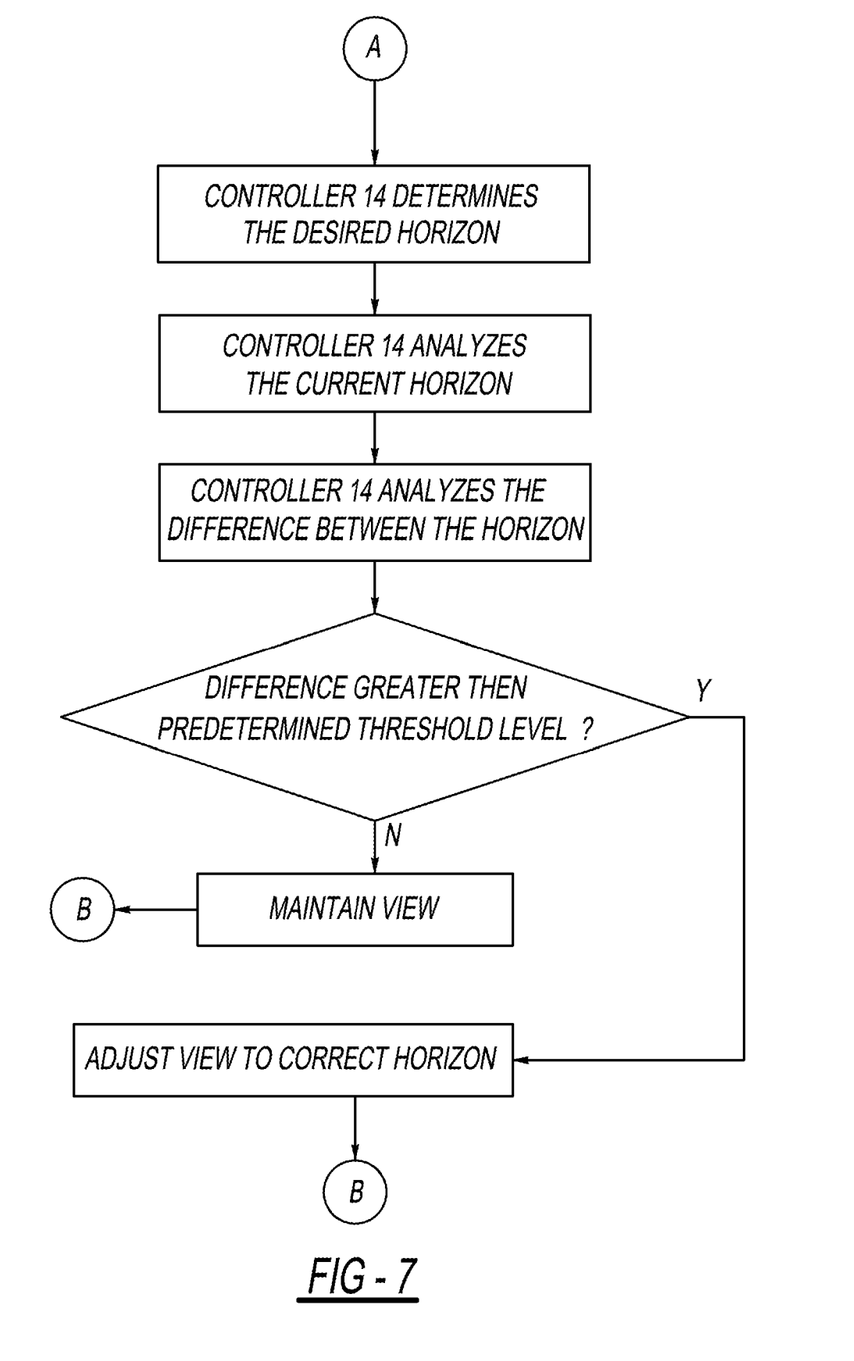
FIG. 7 is a flow chart illustrating a portion of the operation of another aspect of the system.

With reference to FIG. 7, to determine whether horizon correction is necessary, the current orientation of the camera 12 is determined. The orientation of the camera 12 can be determined in multiple ways. The orientation of the camera 12 can be determined based on kinematic feedback of the robot 20. For example, if the robot 20 has moved or rotated in a certain way, the horizon will be corrected based on the degree to which the robot moved. In another approach, the orientation of the camera 12 can be determined based on an orientation sensor coupled to the camera 12. Additionally, or alternatively, the orientation of the camera 12 can be determined based on image analysis of the video stream provided by the camera 12.

After determining the orientation of the camera 12, the difference between the current orientation and the desired orientation is analyzed. If the difference is greater than a predetermined threshold level, then horizon correction will be performed. If the difference is below the predetermined threshold level, then horizon correction is not performed, similar to how camera movement will not occur when the tools 40 are relative close to the center of the view in some camera control schemes. The predetermined threshold level for horizon correction can vary depending on the determined camera control scheme of the determined subtask.

After determining that horizon correction shall be performed, the horizon correction can be performed in multiple ways. In one approach, if the robot 20 is capable of rotating the camera 12 about its axis, then the robot will physically rotate the camera 12 corresponding to the determined horizon misalignment. Additionally, or alternatively, the controller 14 can use its software and programming to adjust the image that is displayed to the user. This software based correction can be performed even when the camera is physically rotated about all three orthogonal axes.

Horizon correction can be part of the determined camera control scheme. Accordingly, in some control schemes, horizon correction may not be used. In some, physical correction may be used. In others, software correction may be used.

The user may also override the automatic movement of the camera 12 if desired. For instance, if the control scheme includes rules that move the camera 12 as intended by the scheme, the user may wish to deviate from the rules of the control scheme in the event of an unanticipated event, or in the event the user's desires differ from the determined control scheme.

Additionally, the controller 14 can learn from the user and adjust the camera control scheme, or create a new camera control with modified rules based on the movements of the user and/or any manual adjustments performed by the user.

As described above, the controller 14 applies the rules of the control scheme based, in part, on input parameters such as the location, movement, and orientation of the tools. Accordingly, with reference to FIG. 2, the tools 40 preferably include one or more detectable elements 48. The detectable elements 48 are configured to be easily identifiable by controller 14 when viewed through the camera 12, or otherwise trackable by a 3D world coordinate system. For example, the elements 48 could be one or more particular colors indicating the type of tool 40 or the location of predetermined elements of the tool 40. For example, a blue indicator could indicate a particular dissection or cutting tool 40. A red indicator could indicate the distal tip of the tool 40 and a green indicator could indicate the proximal end or another portion of the tool 40. The elements could be one or more shapes to indicate different tools 40 or portions of tools. The elements could be a combination of colors and shapes. The elements 48 could be in the form of a reflective material or a radiopaque material used alternatively or in addition to the above described colors and shapes. The tools 40 could also be determined by the controller 14 based on their size, shape, and/or profile when viewed by the camera 12, without the use of detectable elements, in some cases.

The detectable elements 48 may also be in the form of magnets, electromagnets, transmitters, or other elements that can be detected without analyzing the image of the camera 12. These types of elements would cooperate with other detection devices that are in communication with the controller 14, such as magnetic field detectors or positioning receivers that receive a transmission from a transmitter. It will be appreciated that other elements could be used to aid the controller 14 in determining the location of the tools 40 such that the controller 14 can analyze the position and types of tools 40 being used in order to use these input parameters to determine the subtask and/or camera control scheme or to apply the rules associated with the determined camera control scheme. The system 10 can also use infrared to track the tools 40.

Figure 8:
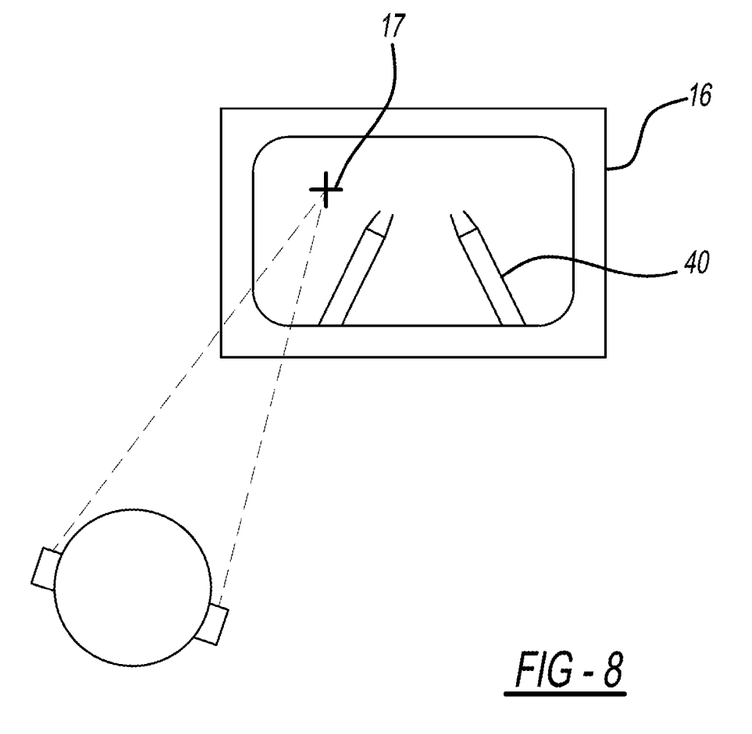
FIG. 8 is a schematic view illustrating a user focusing on an area of the video monitor.

In addition to tracking the tools 40 to ultimately determine how to control the camera 12, the controller 14 can also monitor the movement and position of the user's head and/or eyes. The movement and position of the user's head and/or eyes can indicate the user is focusing on a particular area of the surgical site and, based on the control scheme, may have a rule that instructs the camera 12 to pan and/or zoom in the direction of the user's focus. The screen of the monitor can include cross-hairs 17 to indicate to the user the location of focus that the controller 14 is detecting.

The rules for the various camera control schemes that are associated with the various possible subtasks are determined and programmed into the controller 14 based on interviews and input from various potential users, such as expert surgeons with experience using cameras as part of their procedures. Based on the responses of the surgeons, preferred camera movements related to various input parameters are determined. For example, for a suturing subtask, the surgeons indicate how they would prefer the camera operate for the subtask, whether it should zoom in response to particular tool placement, or whether it should remain stationary at some times or pan or rotate. Based on the responses, rules have been programmed to adjust the camera when certain input parameters are satisfied.

These determinations and rules can be applied to a wide variety of both medical and non-medical procedures where direct visualization is impaired, as well as procedures where direct visualization is possible, if desired. For example, it may be desirable to document a procedure for later review. The automatic control of the camera 12 based on the determined subtasks and camera control scheme increases the efficiency and effectiveness of the operator by reducing the operator's need to control camera.

The features of the subject matter of this case as set forth in the herein above description, the patent claims, the summary, and the drawings, can be important individually or in desired combinations with one another in order to realize the invention in its various forms.

The present invention is, of course, in no way restricted to the specific disclosure of the specification and drawings, but also encompasses any modifications within the scope of the appended claims. The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A system for automatically controlling a camera, the system comprising:
    a controller in the form of a computing device including a processor and a computer readable medium having instructions stored thereon;
    a robotic mechanism operatively coupled to the controller and having the camera attached thereto, wherein the robotic mechanism is capable of receiving commands from the controller for manipulating the camera;
    wherein the controller determines a task to be performed by a surgeon or another user based on first input parameters received at the controller; the task being a medical procedure, a mechanical repair procedure, a procedure for handling of a hazardous material, or a procedure for remote operation for which autonomous camera control can be used;
    wherein the controller automatically determines a pre-determined camera control scheme corresponding to the determined task; the camera control scheme includes programmed algorithms that are pre-determined from the user's preference and requirements regarding the performance of the task; the camera control scheme further including pre-determined rules for controlling the robotic mechanism;
    wherein the controller receives second input parameters;
    wherein the robotic mechanism automatically performs at least one adjustment to the camera selected from the pre-determined rules in response to the controller receiving second input parameters
    wherein a video image from the camera is receivable by the controller;
    wherein the controller is configured to determine a current horizon and a desired horizon for the field of view of the camera such that the current horizon of the field of the camera can be adjusted if the difference between the current horizon and the desired horizon exceeds a predetermined threshold level.

2. The system of claim 1, wherein the first input parameters include a type of tool.

3. The system of claim 1, wherein the first input parameters include a type of procedure.

4. The system of claim 1, wherein the second input parameters are a movement of a tool.

5. The system of claim 1 further comprising a camera attached to the robotic mechanism.

6. The system of claim 5, wherein the robotic mechanism automatically moves the camera based on the second input parameters and the rules of the control scheme.

7. The system of claim 6, wherein the second input parameters include a position of a tool within a field of view of the camera.

8. The system of claim 6, wherein the second input parameters include a position of an area of interest within a field of view of the camera.

9. The system of claim 6, wherein the second input parameters include a position of the current horizon within the field of view of the camera.

10. A method for automatically controlling the movement of a camera, the method comprising:
   receiving, at a controller comprising a computer device having a processor and a computer readable medium having instructions stored thereon, first input parameters;
   determining, at the controller, a pre-defined task to be performed by a surgeon or another user based on the input parameters; the task being a medical procedure, a mechanical repair procedure, procedure for handling of a hazardous material, or a procedure for remote operation for which autonomous camera control can be used;
   determining, at the controller, a pre-defined camera control scheme corresponding to the task, wherein the pre-defined camera control scheme includes programmed algorithms that are pre-determined from the user's preference and requirements regarding the performance of the task; the camera control scheme further including pre-determined rules for controlling the robotic mechanism;
   receiving, at the controller, second input parameters;
   determining, at the controller, a movement command based on the second input parameters, wherein the movement command corresponds to an individual rule of the plurality of pre-defined rules, wherein the individual rule is determined based on the second input parameters;
   automatically moving a robotic mechanism attached to the camera in accordance with the movement command in order to adjust the camera;
   receiving, at the controller, a video image from the camera attached to the robotic mechanism;
   determining, by the controller, a desired horizon for the field of view of the camera;
   determining, by the controller, the current horizon; and
   adjusting the horizon of the field of the camera if the difference between the current horizon and the desired horizon exceeds a predetermined threshold level.

11. The method of claim 10, wherein the first input parameters are a pre-defined task.

12. The method of claim 10, wherein the first input parameters are a type of tool detected by the controller via the video image.

13. The method of claim 10, wherein the second input parameters are a position of a tool detected by the controller via the video image.

14. The method of claim 10 further comprising determining, at the controller via the video image, that two tools are near the center of the video image and, in response thereto, zooming in on the camera based on the rules of the control scheme.

15. The method of claim 10 further comprising determining, at the controller via the video image, that two tools are near opposite edges of the video image and, in response thereto, zooming out on the camera based on the rules of the control scheme.

16. The method of claim 10 further comprising:
   determining, at the controller via the video image, a centroid of two tools;
   determining a position of the centroid within the video image and determining a difference between the position of the centroid and the center of the video image;
   determining that the difference exceeds a pre-determined level; and
   moving the camera to position the centroid near the center of the image such that the difference falls below the pre-determined level.

17. The method of claim 10, further comprising determining, by the controller via a video image from the camera, that a tool is outside the field of view and, in response thereto, stopping movement of the camera.

18. The method of claim 10 further comprising determining, by the controller via a video image from the camera, that tools are moving within the field of view of the camera and maintaining the view of the camera in accordance with the rules of the control scheme.

* * * * *